United States Patent [19]

Lang et al.

[11] Patent Number: 4,528,283

[45] Date of Patent: Jul. 9, 1985

[54] COSMETIC COMPOSITION BASED UPON CHITOSAN DERIVATIVES, NEW CHITOSAN DERIVATIVES AS WELL AS PROCESSES FOR THE PRODUCTION THEREOF

[75] Inventors: Günther Lang, Mühltal; Harald Wendel, Ober-Ramstadt; Eügen Konrad, Darmstadt, all of Fed. Rep. of Germany

[73] Assignee: Wella Aktiengesellschaft, Darmstadt, Fed. Rep. of Germany

[21] Appl. No.: 507,124

[22] Filed: Jun. 23, 1983

[30] Foreign Application Priority Data

Jun. 23, 1982 [DE] Fed. Rep. of Germany ....... 3223423

[51] Int. Cl.³ .......................... A61K 7/48; A61K 7/06; C08B 37/08
[52] U.S. Cl. ..................................... 514/55; 514/844; 514/846; 514/852; 514/880; 514/881; 536/20
[58] Field of Search .......................... 424/70, 358, 365; 536/20; 514/55, 852, 880, 881, 844, 846

[56] References Cited

U.S. PATENT DOCUMENTS

| | | | |
|---|---|---|---|
| 3,879,376 | 4/1975 | Vanlerberghe et al. | 536/20 |
| 3,953,608 | 4/1976 | Vanlerberghe et al. | 536/20 |
| 4,134,412 | 1/1979 | Gross et al. | 536/20 |
| 4,307,079 | 12/1981 | Zorayan et al. | 424/365 |
| 4,402,977 | 9/1983 | Grollier et al. | 424/70 |

FOREIGN PATENT DOCUMENTS 11955  1/1979  Japan ..................................... 536/20

*Primary Examiner*—Johnnie R. Brown
*Attorney, Agent, or Firm*—Michael J. Striker

[57] ABSTRACT

Cosmetic compositions useful for treatment of hair or skin contain macromolecular glyceryl-chitosan having (a) 4–40 Mol-% units of the Formula (I)

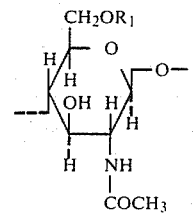

and
(b) 60–96 Mol-% units of the Formula (II)

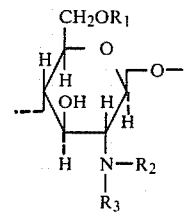

wherein $R_1$, $R_2$ and $R_3$ are the same or different and are

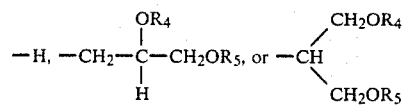

wherein $R_4$ and $R_5$ are the same or different and are

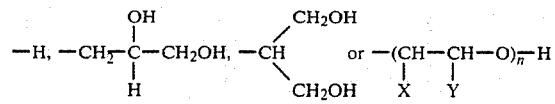

wherein either X=H and Y=CH₂OH, or Y=H and X=CH₂OH and n=2 to 5, with the proviso that for at least half of the units of the formula II, $R_1$, $R_2$ and $R_3$ are not uniformly H, or their salts with organic or inorganic acids, in a suitable cosmetic carrier. Also disclosed are the compounds per se and a process for their production wherein chitosan composed of 60–96% entacetylated chitin is reacted with glycidol.

16 Claims, No Drawings

COSMETIC COMPOSITION BASED UPON CHITOSAN DERIVATIVES, NEW CHITOSAN DERIVATIVES AS WELL AS PROCESSES FOR THE PRODUCTION THEREOF

BACKGROUND OF THE INVENTION

The invention concerns cosmetic compositions for the treatment of hair or skin, having a content of new macromolecular compounds derived from chitosan, which in aqueous or water-alcoholic preparations are employed, if necessary, with further additives. They are useful with humans, or even animals.

The invention also concerns new glyceryl-chitosan, i.e. macromolecular, compounds derived from chitosan, as well as processes for their production.

It is already known to employ cation-active polymers, particularly polymers which display quaternary ammonium groups, as conditioners in cosmetic compositions, particularly for the treatment of hair. On the basis of an interaction between their ammonium groups and the anionic groups of the hair, the cation-active polymers possess a great affinity for keratin fiber.

It has been determined that upon employment of such cation-active polymers in cosmetic compositions of this type, numerous advantages are provided. Disentanglement of the hair as well as its handling are facilitated, and, in addition, the hair is provided with bounce (elastic force) and lustre. Through the affinity towards keratin these polymers tend, however, upon repeated use, to accumulate on the hair, so that it becomes heavier, which as an end result is undesirable.

Moreover, with synthetic polymers, problems arise on account of the physiological activity of possibly present monomer traces, which can be removed from the polymer only with difficulty.

It has already been attempted to eliminate the above mentioned disadvantages by using in such cosmetic compositions water-soluble salts of chitosan, polyglucosamine prepared by entacetylation from chitin. In this connection, reference is made to European Pat. No. 0 002 506, as well as German Pat. No. 26 27 419, which are hereby incorporated by reference.

In similar manner as with the plurality of cation-active polymers having quaternary groupings, chitosan likewise frequently provides the disadvantage that it is only slightly compatible with the anion-active surface-active agents which are customarily used in cosmetic compositions for the treatment of hair, particularly shampoos. It is therefore necessary to apply the chitosan in separate treatments, namely before and/or after the shampooing.

The chitosan proves, moreover, to be practically insoluble in neutral and alkaline media, whereby its use, for example, in alkaline permanent compositions or hair dye compositions is not possible.

SUMMARY OF THE INVENTION

It is therefore an object of the present invention to eliminate the above discussed disadvantages.

Upon performance of tests with chitosan and the compounds derived therefrom, it has been found that certain chitosan derivatives, and indeed specific glyceryl-chitosans, do not display the previously set forth disadvantages.

In particular, this object according to the present invention is attained with glyceryl-chitosan or their salts with organic or inorganic acids, which allow for the production of cosmetic compositions for the treatment of hair or skin and which distinguish through surprisingly advantageous characteristics and are characterized by a content of glyceryl-chitosan, and indeed macromolecular compounds derived from chitosan, composed of:

(a) 4–40 Mol-% units of the Formula (I)

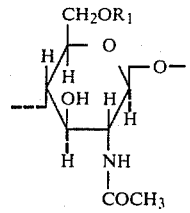

and (b) 60–96 Mol-% units of the Formula (II)

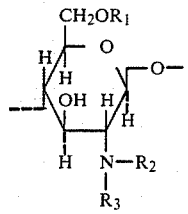

wherein $R_1$, $R_2$ and $R_3$ are the same or different and are

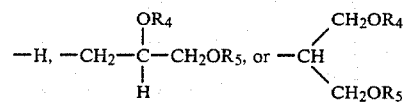

wherein $R_4$ and $R_5$ are the same or different and are

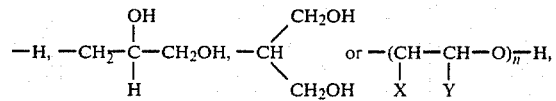

wherein either $X=H$ and $Y=CH_2OH$, or $Y=H$ and $X=CH_2OH$ and $n=2$ to $5$, with the proviso that for at least half of the units of Formula II, $R_1$, $R_2$ and $R_3$ are not uniformly H, or their salts with organic or inorganic acids, in a suitable cosmetic carrier.

The salts of glyceryl-chitosan according to the present invention can be obtained for example by neutralization of the amino groups of the glyceryl-chitosans with acid(s). However, according to the present invention only such salts can be employed which are soluble in water. Suitable salts include, for example, those that are formed with the acids lactic acid, formic acid, and acetic acid.

The compositions containing glyceryl-chitosan according to the present invention are suitable in general for the treatment of hair and/or skin. They can be provided, for example, as hair washes and/or body washes, coloring shampoos, hair dressing creams, hair tonics, blow-dry lotions, hair setting lotions, wash lotions, hair conditioners, anti-dandruff agents, agents for permanent hair deformation, agents for the coloring or decoloring of hair, agents for applying before or after the hair coloring, and as cosmetic agents for the care, for the protection, or for the cleaning of the skin, such as so-called facial tonic, shaving lotion, moisture-holding creams or moisturizers, cold creams, body lotions, sun-screens or also makeup preparations such as greasepaint creams and rouges.

The cosmetic compositions according to the present invention can additionally contain, aside from the new glyceryl-chitosan, all such components as are customarily employed in hair and skin treatment compositions, in particular anionic, cationic, amphoteric, zwitterionic or non-ionic surface-active tensides, foam synergists, stabilizers, sequestrants, pigments, thickeners, emulsifiers, buffer substances, preservatives, dyes, perfume oils, known cosmetic polymers such as anionic, non-ionic, cationic or amphoteric polymers, natural substances, cosmetic oils, fatty alcohols, waxes, foam stabilizers, anti-dandruff substances, reducing agents and propellant gas.

The cosmetic compositions according to the present invention display in preferred manner a pH-value from 2 up to 11 and can be provided in the form of aqueous preparations, water-alcoholic preparations, e.g. with an alcohol having 1 up to 4 carbon atoms, as solutions, as creams, as gels, as dispersions, or as emulsions. It is likewise possible to spray these compositions with the aid of an atomizer or other suitable spraying arrangements, or, in mixture with customary propellant gas, from a pressure container.

When the cosmetic compositions according to the present invention are concerned with the strengthening or fixing of hairdos, such as is the case with liquid hair strengtheners or hair sprays, they can be provided in customary manner as aqueous or water-alcoholic solutions, which are characterized by a content of glyceryl-chitosan composed from units of the above set forth Formulas I and II or their soluble salts with organic or inorganic acids. Herewith the glyceryl-chitosan itself is employed as film-forming or fixing resin. The preparations can also contain, in addition, other film-forming natural or synthetic polymers in hair strengthening compositions according to the present invention. Natural polymers coming into consideration can include, for example, shellac, alginate, gelatin, pectin and cellulose derivatives. Synthetic polymers that may be employed include, e.g., polyvinyl pyrrolidone, polyvinyl acetate, polyacryl compounds, such as acrylic acid- or methacrylic acid polymerisates, basic polymerisates of esters of acrylic acid or methacrylic acid with aminoalcohols or the salts or quaternization products of these basic polymerizates, polyacrylonitrile as well co- or ter(tiary) polymerisate of such compounds, for example polyvinyl pyrrolidone-vinylacetate.

Alcohols particularly coming into consideration for the cosmetic purpose include customarily employed lower alcohols such as ethyl alcohol and isopropyl alcohol.

The compositions according to the present invention for the strengthening of hairdos can moreover contain the customary additives, such as for example perfume oils, bactericides or fungicides, combability-improving substances, among others.

The compositions according to the present invention for the strengthening of hairdos or settings can, if necessary, color or shade the hair at the same time, by means of a content of cosmetic dyes. Such preparations are commercially designated as color-settings, among others. They contain, additionally, dyes customarily known for color-settings such as, for example, aromatic nitro-dyes (e.g., 1,4-diamino-2-nitrobenzene), azo-dyes (e.g., C.I. Acid Brown 4), anthraquinone dyes (e.g., C.I. Disperse Violet 4) and triphenylmethane dyes (e.g., C.I. Basic Violet 1), whereby the dyes of these classes, indeed according to the type of their substituents, can have acid, non-ionogenic or basic character. Their total concentration in these preparations customarily amounts to between 0.01 and 2.0% by weight.

The compositions according to the present invention for the strengthening or setting display, with the same good strengthening of the hair in contrast to customary compositions, a particularly good combability and a good grip of the hair in the wet state, as well as a particularly pleasant feel of the hair in the dry state. If the compositions according to the present invention are to represent hair washes, they are provided in the form of aqueous solutions or emulsions and contain, in addition to the glyceryl-chitosan, at least one anionic, cationic, non-ionic or amphoteric tenside.

The concentration of the tenside in these hair washes generally amounts to between about 3 and 50% by weight and preferably between about 3 and 20% by weight, relative to the total weight of the composition. The pH-value is generally maintained at between about 3 and 9 and preferably between about 4 and 7.

The compositions according to the present invention that are provided in the form of hair washing agents generally contain various additives, in particular perfumes, preservatives, thickeners, foam stabilizers, buffer substances, cosmetic resins, pigments and dyes.

Under the designation "foam stabilizers", mention should be made of the fatty amides and, in particular, the mono- or di-ethanolamides of copra fatty acids, lauryl- or oleic acid mono- or diethanol amides, which expediently are employed in amounts from about 1 up to 10 and preferably 1 up to 3% by weight, relative to the total weight of the compositions.

Useful thickeners include, in particular, the acryl polymers and the cellulose derivatives such as carboxymethyl cellulose, hydroxypropylmethyl cellulose, hydroxyethyl cellulose. The thickeners are generally provided in a portion from about 0.1 up to 5% by weight.

Tensides or surface-active agents which, in combination with the new glyceryl-chitosans, can be employed according to the present invention include, for example, the following:

(a) the anionic surface-active agents, such as for example the alkali- or earth-alkali salts or alkanolamines of alkane sulfonates, alkyl sulfates and alkylether sulfonates, the $C_{12}$–$C_{18}$-alkyl- and particularly $C_{12}$–$C_{14}$-alkyl-sulfate sodium salts or triethanolamine salts, the sodium- or triethanolamine salts of lauryl- or tetradecylether sulfates, the disodium salt of sulfosuccinic-semiester of alkanolamides, the soaps and the polyether-carboxylic acids;

(b) the non-ionic surface-active agents, such as for example oxethylated fatty alcohols with 12 up to 18 carbon atoms, e.g., with up to 40 Mol ethylene oxide per Mol fatty alcohol, oxethylated lauric-, tetradecyl-, cetyl-, oleic-, palmitic- and stearic alcohol, alone or in mixture, the fatty alcohols of oxethylatable lanolin or oxethylated lanolin; polyglycerylether of saturated or unsaturated fatty alcohols and alkylphenols with 8 up to 30 carbon atoms in the alkyl group and 1 up to 10 glyceryl units in the molecule, as well as fatty acid alkanolamide;

(c) the cationic surface-active agents, such as for example the dilauryldimethylammonium chloride, the chloride or bromide of alkyldimethylbenzylammonium, the chloride or bromide of alkyltrimethylammonium, for example cetyltrimethylammonium chloride or -bromide, tetradecyltrimethylammonium chloride or -bromide, the alkyldimethylhydroxyethylammonium chloride or -bromide, the dialkyldimethylammonium chloride or -bromide, alkylpyridinium salt, for example cetylpyridinium chloride, the alkylamidethyltrimethylammoniumether sulfate, imidazoline derivatives, compounds with cationic character such as aminoxide, for example alkyldimethylaminoxide or alkylaminoethyldimethylaminoxide;

(d) the amphoteric or zwitterionic surface-active agents such as for example the carboxyl derivatives of imidazole, the N-alkylbetains, the N-alkylsulfobetains, the N-alkylaminobetains, the N-alkylaminopropionates, the alkyldimethylammonium acetates or the $C_{12}-C_{18}$-alkyldimethylcarboxymethylammonium salts.

The cosmetic compositions according to the present invention can also represent creams or lotions for use as hair conditioning or skin care agents. In this case they are provided mainly in the form of oil-in-water or water-in-oil emulsions or suspensions, and contain, in addition to the new glyceryl-chitosan, cationic, non-ionogenic, amphoteric or anionic emulsifiers as well as, as component of the oil phase, fatty alcohols, fatty acid-ester or -amide, moreover perfume oils, vaseline, wool grease alcohol (lanolin) or solid or liquid wax.

When the compositions according to the present invention represent hair shading or hair coloring agents, they are likewise provided preferably in the form of creams or lotions and contain, additionally, customary hair dyes from the group of the aromatic nitro-dyes, azo-dyes, anthraquinone-dyes, triphenylmethane-dyes or also oxidation dyes, for example from the group of the aromatic diamides or aminophenols. Moreover, these compositions can contain, if necessary, alkylization agents, antioxidants as well as further cosmetic additives and adjuvants customary for such compositions.

The compositions according to the present invention can also represent permanent deformation agents or fixing agents for the hair. They then contain, in addition to the mentioned glyceryl-chitosans, reducing agents such as thioglycolic acid, thiolactic acid, ammonium sulfite or oxidation agents, such as hydrogen peroxide or sodium bromate as well as, if necessary, alkylization agents or peroxide stabilizers, e.g. phosphoric acid, and other cosmetic adjuvants and additives such as for example perfume oils, odorous substances, care substances and dyes.

The content of glyceryl-chitosan in the cosmetic compositions according to the present invention expediently amounts to between about 0.05 up to 10% by weight, preferably 0.05 up to 3.0% by weight.

The new chitosan derivatives contained in the cosmetic compositions according to the present invention are derived from chitosan, a material which is obtained through deacetylation of chitin, a naturally occurring acetylglucosamine.

The chitosan is insoluble in neutral and alkaline media, but forms, however, based upon its chemical nature, in acid media with organic and inorganic acids, salts, which are used for example in the paper and textile industries as additives. The salts can be used, moreover, as coagulants for suspensions, as gelation adjuvants for heavy metals, as well as in medicine and in cosmetics. (In this connection, reference is made to the Muzarelli publication: "Chitin", Pergamon Press, 1977.)

Several water-soluble chitosan derivatives are already known, for example carboxymethyl chitosan and sulfoethyl chitosan (see, e.g., Nud'ga, Plisko and Darnilov, Zhur.Prikl. Khim. 47, 872–875). These water-soluble chitosan derivatives are, however, altered in their ionic character, or even physiologically harmful (Epichlorhydrinchitosan, publication of Noguchi, Arato and Komai; Kogyo Kagaku Zasshi 72, 796-799 and Japanese Patent Application No. 46-39 322, H. Haga).

A further noteworthy factor is that these mentioned substances require expensive techniques for their technical production.

The reaction of glycidol with primary amines is known in principle from the publication of A. Kleeman, R. Wagner "Glycidol, Properties, Reactions, Applications", Hüthig Verlag 1981, pp. 84 ff. Reactions of the glycidol with amino-group-containing polymers have not, however, been previously described.

It has been discovered that through reaction of chitosan with glycidol, new chitosan derivatives can be produced in simple manner, and which with suitable degree of substitution are well soluble in water and possess outstanding film characteristics.

With this reaction, the amino-groups of the glucosamine unit reacts in the first place with the glycidol(1,2-epoxypropanol-3 or glycerine anhydride); furthermore, a substitution to the primary alcohol group can follow in the 2-position.

The new macromolecular compounds derived from chitosan are characterized in that they are composed of (a) 4–40 Mol-% units of Formula (I)

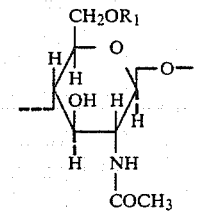

(b) 60–96 Mol-% units of the Formula (II)

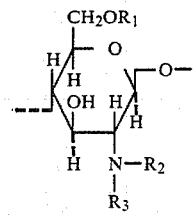

wherein $R_1$, $R_2$ and $R_3$ are the same or different and are

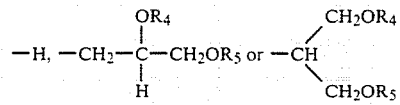

wherein $R_4$ and $R_5$ are the same or different and are

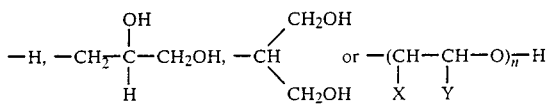

wherein either $X=H$ and $Y=CH_2OH$, or $Y=H$ and $X=CH_2OH$ and $n=2$ to 5, with the proviso that for at least half of the units of Formula II, $R_2$ and $R_3$ are not uniformly H, or their salts with organic or inorganic acids.

The new glyceryl-chitosans are produced according to the present invention by reacting a chitosan, composed of chitin entacetylated to 60–96%, with glycidol(1,2-epoxypropanol-3) in suitable ratio.

For this purpose the chitosan is expediently employed in finely pulverized form. The reaction itself can take place at temperatures between about 10° and 100° C., preferably between 50° and 80° C. The temperature may be appropriately maintained with stirring for 2 to 100 hours. The reaction can follow with or without acid or basic catalyst, in the presence of solvent or without solvent.

Preferably, the reaction is performed in the presence of water. Therewith it has proven to be advantageous to work without additional catalyst, whereby the ratio of chitosan to water lies between 1:0.05 and 1:100, and the ratio of chitosan to glycidol (relative to the mols of substitutable amino groups at the chitosan) lies between 1:0.5 and 1:30, preferably between 1:1 and 1:10.

Although the reaction is favorably performed in the presence of water, it can also take place using another solvent, in which at least one of the reaction products is soluble. Examples for such solvent include alcohols such as ethanol, methanol, glycol and glycerine, as well as ketones, for example methylethylketone and acetone.

According to another embodiment of the process according to the present invention for the production of glyceryl-chitosans, additional organic or inorganic acids or bases are added as catalyst for the reaction.

Acids suitable for employment as catalyst include, for example, hydrochloric acid, lactic acid and formic acid. Examples of suitable bases include trialkylamines such as trimethylamine, triethylamine, or trialkylolamine, as well as alkali hydroxide and earth alkali hydroxide. It is also possible, in principle, to start from water-soluble salts of chitosan, for example chitosan lactate, chitosan acetate, chitosan hydrochloride, among others. In connection therewith, a greater amount of the glycerine ester of the employed acid can, however, be produced as by-product, so that the cleaning of the reaction products is made more difficult.

Working up of the reaction mixture can follow, for example, by distilling off the solvent and, if necessary, excess glycidol, in a vacuum.

With the production of water-soluble glyceryl-chitosans the reaction product can, favorably, be dissolved in an excess in water, and then separated from non-soluble reaction residue by means of filtration or centrifugation. A suggested further step for purification of the reaction product is to dialyze the aqueous solutions and/or, if necessary after concentrating the aqueous solutions, isolating by means of precipitation in acetone, alcohols or other organic solvents.

Chitosan modified structurally through reprecipitation and deep-freezing, is employed as starting material according to a particularly advantageous embodiment of the production technique according to the present invention. The reaction proceeds in particularly advantageous manner and with particular good yields when such starting materials are employed.

The novel features which are considered characteristic for the invention are set forth in particular in the appended claims. The invention itself, however, both as to its construction and its method of use, together with additional objects and advantages thereof, will be best understood from the following description of specific embodiments.

DESCRIPTION OF THE PREFERRED EMBODIMENTS

EXAMPLE 1

12 g chitosan having a limit viscosity number $\eta=140$ ml/g (determined in a DIN-Ubbelohde viscosimeter with 0.2 m acetic acid and 0.1 m sodium acetate as solvent) and a free amine content of 86% are reacted with 24 ml glycidol (mol-ratio 1:4.5).

The content of free amine is determined by means of potentiometric titration in water-free acetic acid as solvent, using 0.1 m perchloric acid in water-free acetic acid.

The reaction is performed in a two-neck round flask at a temperature in the range from 20°–60° C. The reaction period is 30 hours.

Thereafter the batch becomes so thickened that it is no longer stirrable.

The reaction mixture is then placed in 1 liter water to dissolve the water-soluble portion. The insoluble residue is separated by filtration or centrifugation. The aqueous solution is then concentrated in a vacuum to about 200 ml, and the reaction product is then precipitated in 2 l acetone. After drying in a vacuum at 50° C., 11.5 g of a clear water-soluble chitosan derivative is obtained.

Characteristic data of the reaction product:
Limit (Critical) Viscosity Number: $\eta=67$ ml/g
Titratable Nitrogen: 3.3 mmol/g
Degree of Substitution Determined Thereby: 1.44

Upon drying, the aqueous solution forms a clear, elastic film.

EXAMPLE 2

100 g chitosan ($\eta=140$ ml/g; 86% free amine) are reacted with 450 ml glycidol (mol ratio 1:9) in a double jacketed stirrer vessel and stirred for 96 hours at temperatures in the range from about 20° up to 60° C. The reaction product is placed in about 5 l water, and the insoluble residue is centrifuged off.

The aqueous solution is concentrated, and the reaction product is isolated by precipitation in acetone.

After drying in a vacuum at 50° C. a yield of 60 g is obtained. A portion of the substance is dissolved again in water and dialyzed for 1 week. (Dialysis tubing separation limit = 1000).

Characteristic Data of the Reaction Product:

|  | (a) not dialyzed | (b) dialyzed |
|---|---|---|
| Limit Viscosity (ml/g): | 44 | 33 |
| Titratable Nitrogen: | 2.7 mmol/g | 3.1 mmol/g |
| Degree of Substitution Therefrom: | 2.4 | 1.7 |

Upon drying, the aqueous solutions provide elastic film. The water vapor absorption amounts to 10% by weight with 80% air moisture compared to 30% air moisture. The pendulum hardness (determined by the method according to Koenig) is 185 sec.

EXAMPLE 3

The following four tests illustrate the influence of solvent and catalyst. A chitosan with characteristic data $\eta = 140$ ml/g and 86% free amine is employed.

(a) 10 g chitosan are pre-swollen overnight in 50 ml water and then removed by suction. The moist chitosan is then placed into reaction.

(b) 10 g chitosan are placed overnight in 50 ml water and pre-swollen. It is then placed into reaction with the water as solvent.

(c) 10 g chitosan are pre-swollen overnight with 10 g 10% lactic acid and 40 ml water. It is then placed into reaction.

(d) 10 g chitosan are placed into reaction in a solution composed of 100 ml ethylene glycol and 1 mm tripropylamine.

The reactions are performed at room temperature, each with 40 ml glycidol. Half of each sample is worked up after 1 day, the remainder after 5 days.

| Yield after: | a | b | c | d |
|---|---|---|---|---|
| 1 day | 1 g | 1.5 g | 2 g | — |
| 5 days | 6 g | 4 g | 3.5 g | 6.5 g |

Characteristic Data of the Reaction Product:

| | | a | b | c | d |
|---|---|---|---|---|---|
| Degree of Substitution Determined from Titratable N: | 1 day | 1.8 | 2.2 | 2.5 | — |
| | 5 days | 1.7 | 2.2 | 2.5 | 1.6 |
| Limit Viscosity Number $\eta$ in ml/g: | 5 days | 36 | 30 | 52 | 51 |

EXAMPLE 4

This Example employs chitosan samples with different degrees of entacetylation:
Chitosan
(a) $\eta = 140$ ml/g, free $NH_2 = 86\%$
(b) $\eta = 1100$ ml/g, free $NH_2 = 62\%$
For each test, 10 g chitosan are reacted with 13.3 ml glycidol. At room temperature, the period of reaction is 4 days.
Yields: (a) 6.5 g, (b) 3.5 g
Characteristic Data of the Obtained Reaction Product:

| Limit Viscosity Number $\eta$: | (a) 69 ml/g | (b) 201 ml/g |
|---|---|---|
| Degree of Substitution Determined from Titratable N: | 1.8 | 1.9 |

The aqueous solutions provide clear, elastic film. The water vapor absorption at 80% air moisture in contrast to 30% air moisture amounts to 10% by weight.
Pendulum Hardness (a.t. Koenig): (a) 170 sec, (b) 160 sec.

EXAMPLE 5

40 g chitosan ($\eta = 650$ ml/g; 75% free amine) are reacted with 67 g glycidol (mol ratio 1:3). This is done in two stages. First, 44 g glycidol are added and the mixture is stirred for 24 hours at room temperature. Then the remaining 23 g glycidol are added, followed by stirring at room temperature for 72 hours. The reaction product is subsequently dissolved in water, and the solution is adjusted with hydrochloric acid to a pH of 4.2.

The solution is then apportioned: One part is dialyzed for 1 week; the remainder is worked up as described in Example 1.

Characteristic Data of the Reaction Product:

| | analyzed | not dialyzed |
|---|---|---|
| Yields: | 22.7 g | 32 g |
| Limit Viscosity Number $\eta$: | 203 ml/g | 231 ml/g |
| Degree of Substitution Determined from Titratable N: | 3.1 | 7.1 |

Upon drying, the aqueous solutions provide clear, elastic film. The water vapor absorption amounts to 9%. Pendulum hardness according to Koenig is 150 sec.

EXAMPLE 6

10 g chitosan ($\eta = 140$ ml/g; 86% free amine) are dissolved in hydrochloric acid and then filtered. The chitosan is then precipitated from the filtrate with caustic soda. The finely dispersed precipitate is vacuum evacuated and placed overnight in deep freeze. The sample is then defrosted, once again vacuum evacuated and brought to reaction with 16 g glycidol at 80° C. After 3 hours the batch is dissolved clear and highly viscous.

The substance is then precipitated in acetone and dried in a vacuum at 50° C. The yield amounts to 11 g.
Characteristic Data of the Reaction Product:
Limit Viscosity Number $\eta$: 100 ml/g
Degree of Substitution Determined from Titratable N: 2.2

The following examples are for cosmetic compositions based upon the new glyceryl-chitosan compounds according to the present invention:

EXAMPLE 7

| Hair Setting Lotion | |
|---|---|
| 0.6 g | glyceryl-chitosan ($\eta = 33$ ml/g, degree of substitution = 1.7) |
| 73.8 g | water |
| 25.0 g | isopropanol |
| 0.4 g | 10% formic acid |
| 0.2 g | perfume oil |
| 100.0 g | |

20 ml of this solution are distributed onto washed, towel-dried hair. The hair is then set in customary manner and dried. With better strengthening effectiveness, the hair, when compared with results using a hair setting lotion based upon chitosan/formic acid, has a more agreeable and softer feel.

EXAMPLE 8

| Color Setting Lotion | |
|---|---|
| 1.00 g | glyceryl-chitosan ($\eta = 201$ ml/g, degree of substitution = 1.9) |
| 1.00 g | lactic acid |
| 0.10 g | cetyltrimethylammonium chloride |
| 0.05 g | Acid Brown 4 (C.I. 41 805) |

-continued

| Color Setting Lotion | |
|---|---|
| 97.85 g | water |
| 100.00 g | |

20 ml of this solution are distributed onto washed, towel-dried hair, and the hair is then arranged in customary manner and dried. The hair subsequently displays a light red-brown coloration.

EXAMPLE 9

| Color Setting Lotion | |
|---|---|
| 0.60 g | glyceryl-chitosan ($\eta$ = 203 ml/g, degree of substitution = 3.1) |
| 0.15 g | 1,4-di($\beta$-hydroxyethylamino)-2-nitro-5-chlorobenzene |
| 25.00 g | ethanol |
| 74.25 g | water |
| 100.00 g | |

20 ml of this solution are placed onto washed, hand towel-dried hair, after which the hair is arranged and dried. The result is that the hair becomes colored red-violet and strengthened.

EXAMPLE 10

| Anionic Hairwash | |
|---|---|
| 1.00 g | glyceryl-chitosan ($\eta$ = 52 ml/g, degree of substitution = 2.5) |
| 40.00 g | lauryl alcohol diglycolether sulfate-sodium salt, 28% aqueous solution |
| 4.00 g | sodium chloride |
| 0.05 g | dye |
| 54.85 g | water |
| 0.10 g | formaldehyde, 25% aqueous solution |
| 100.00 g | |

A clear shampoo is obtained. Hair washed with the shampoo becomes excellently conditioned with regard to grip, lustre and combability.

EXAMPLE 11

| Amphoteric, Coloring Hairwash | |
|---|---|
| 2.00 g | glyceryl-chitosan ($\eta$ = 67 ml/g, degree of substitution = 1.44) |
| 40.00 g | dimethyl-carboxymethylene-propyleneamido-stearate-betaine, 35% aqueous solution |
| 5.06 g | formic acid, 10% |
| 3.50 g | cocos fatty acid diethanolamide |
| 1.00 g | picramic acid (C.I. 76 540), 1% aqueous solution |
| 48.44 g | water, completely desalted |
| 100.00 g | |

The hair is shampooed with about 15 to 20 g of the hairwash. After a working-in period of 5 to 10 minutes, the hair is rinsed with water. The result is that the hair is toned yellow-orange and excellently conditioned.

EXAMPLE 12

| Hair Treatment Composition, Cationic | |
|---|---|
| 0.30 g | glyceryl-chitosan ($\eta$ = 44 ml/g, degree of substitution = 2.4) |
| 4.00 g | cetylstearyl alcohol |

-continued

| Hair Treatment Composition, Cationic | |
|---|---|
| 1.48 g | lactic acid, 10% |
| 2.50 g | cocos (pentaethoxy) methylammonium chloride |
| 1.00 g | sorbitane monopalmitate with 20 mol ethylene oxide |
| 90.72 g | water, completely desalted |
| 100.00 g | |

EXAMPLE 13

| Hair Conditioning Composition, Gel | |
|---|---|
| 2.1 g | glyceryl-chitosan ($\eta$ = 33 ml/g, degree of substitution = 1.7) |
| 0.6 g | hydroxypropylmethyl cellulose |
| 0.5 g | lauryl pyridinium chloride |
| 96.8 g | water, completely desalted |
| 100.0 g | (adjusted to pH 5.0, with 10% formic acid) |

In each case, 35 g of the hair conditioning composition according to Examples 12 and 13 are distributed onto washed hair and, after a working-in period of 3 to 5 minutes, rinsed again with water. The results are that an excellent grip, lustre and combability of the hair are obtained.

EXAMPLE 14

| Skin Cream | |
|---|---|
| 0.30 g | glyceryl-chitosan ($\eta$ = 33 ml/g, degree of substitution = 1.7) |
| 3.00 g | stearyl alcohol |
| 1.00 g | wool fat alcohol (*adeps lanae*) |
| 1.00 g | vaseline |
| 0.76 g | lactic acid, 10% |
| 1.00 g | sodium cetylstearyl sulfate |
| 92.94 g | water, completely desalted |
| 100.00 g | |

EXAMPLE 15

| Hair Toning Agent | |
|---|---|
| 0.50 g | glyceryl-chitosan ($\eta$ = 30 ml/g, degree of substitution = 1.44) |
| 12.00 g | cetylstearyl alcohol |
| 0.10 g | parahydroxybenzoic acid ethyl ester |
| 6.00 g | lauryl alcohol-diglycolether sulfate-sodium salt (28% aqueous solution) |
| 0.50 g | perfume oil |
| 79.31 g | water |
| 0.50 g | 1-hydroxy-2-amino-4-nitrobenzene (C.I. 76 530) |
| 0.85 g | 1,4-diamino-2-nitrobenzene (C.I. 76 070) |
| 0.24 g | sodium hydroxide |
| 100.00 g | |

Approximately 30 to 40 g of the composition are distributed into washed hair and then rinsed off after a working-in period of about 20 minutes. The hair is colored reddish and displays a good combability and a pleasant feel.

EXAMPLE 16

| Oxidation Hair Dye Composition | |
|---|---|
| 0.50 g | glyceryl-chitosan ($\eta$ = 33 ml/g, |

-continued

| Oxidation Hair Dye Composition | |
|---|---|
| | degree of substitution = 1.7) |
| 0.08 g | 3,5-diamino-2,6-dimethoxypyridine-dihydrochloride |
| 0.30 g | 1,4-diaminobenzene |
| 0.25 g | resorcinol |
| 0.30 g | sodium sulfite |
| 3.50 g | lauryl alcohol-diglycolethersulfate-sodium salt (28% aqueous solution) |
| 15.00 g | cetyl alcohol |
| 3.00 g | ammonia |
| 77.07 g | water |
| 100.00 g | |

50 g of this hair dye composition are mixed with 50 ml 6% hydrogen peroxide solution and applied to white hair. After 30 minutes the hair is rinsed with water and dried. The hair has a natural effective matte-blonde coloration as well as a natural, pleasant feel.

EXAMPLE 17

| Permanent Waving Composition | |
|---|---|
| 0.5 g | glyceryl-chitosan ($\eta$ = 203 ml/g, degree of substitution = 3.1) |
| 10.0 g | thioglycolic acid |
| 8.0 g | ammonia, 25% |
| 6.1 g | ammonium hydrogen carbonate |
| 75.4 g | water |
| 100.0 g | |

This permanent waving composition is applied uniformly onto rolled, towel-dried hair, and allowed to work itself in for about 20 minutes. The hair is then rinsed with water and oxidatively treated in known manner. A good wave result is obtained, with the hair feeling natural and soft.

It will be understood that each of the elements described above, or two or more together, may also find a useful application in other types of hair or skin compositions differing from the types described above.

While the invention has been illustrated and described as embodied in a cosmetic composition based upon chitosan derivatives, new chitosan derivatives as well as processes for the production thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Cosmetic composition useful for the treatment of hair or skin, comprising as active agent glyceryl-chitosan composed of macromolecular compounds derived from chitosan and having (a) 4-40 Mol-% units of the Formula (I)

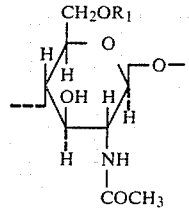

and (b) 60-96 Mol-% units of the Formula (II)

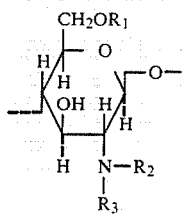

wherein $R_1$, $R_2$ and $R_3$ are the same or different and are

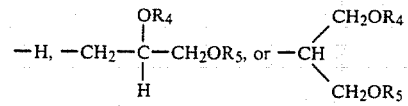

wherein $R_4$ and $R_5$ are the same or different and are

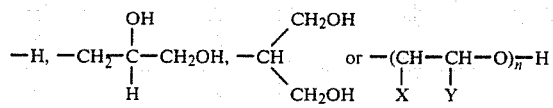

wherein either $X=H$ and $Y=CH_2OH$, or $Y=H$ and $X=CH_2OH$ and $n=2$ to 5, with the proviso that for at least half of the units of the formula II, $R_1$, $R_2$ and $R_3$ are not uniformly H, or their salts with organic or inorganic acids, in a suitable cosmetic carrier.

2. Composition according to claim 1, wherein said glyceryl-chitosan is present in amounts from 0.05 up to 10% by weight.

3. Composition according to claim 1, for use as a hair wash.

4. Composition according to claim 1, further comprising an anionic surface-active substance.

5. Composition according to claim 4, wherein said anionic surface-active substance is an alkylether sulfate.

6. Composition according to claim 1, comprising a hair setting preparation.

7. Composition according to claim 1, further comprising hair dye.

8. Composition according to claim 7, wherein said hair dye is present in an amount from about 0.01 up to 2.0% by weight.

9. Composition according to claim 1, further comprising perfume, preservative, thickener, foam stabilizer, buffer substance, cosmetic resin or pigment.

10. Composition according to claim 1, further comprising reducing agent, oxidation agent, alkalization agent or peroxide stabilizer.

11. Macromolecular compound derived from chitosan, comprising (a) 4–40 Mol-% units of the formula (I)

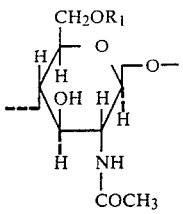

and (b) 60–96 Mol-% units of the formula (II)

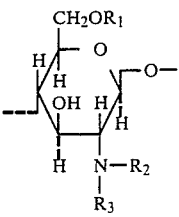

wherein $R_1$, $R_2$ and $R_3$ are the same or different and are

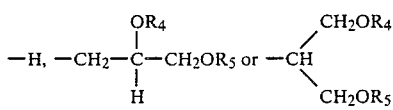

wherein $R_4$ and $R_5$ are the same or different and are

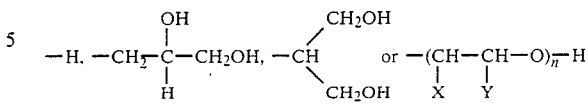

wherein either X=H and Y=CH$_2$OH, or Y=H and X=CH$_2$OH and n=2 to 5, with the proviso that for at least half of the units of the formula II, $R_2$ and $R_3$ are not uniformly H, or its salt with organic or inorganic acid.

12. Process for the production of compounds according to claim 11, comprising reacting chitosan with glycidol at a temperature between 10° and 100° C. for 2 to 100 hours with stirring, wherein said chitosan is provided in finely pulverized form, composed of chitin entacetylated to 60–96%, and the ratio of chitosan to glycidol, relative to the mols of substitutable amino groups in the chitosan, lies between 1:0.5 and 1:30.

13. Process according to claim 12, wherein said reacting is performed in the presence of water.

14. Process according to claim 12, further comprising before said reacting, initially structurally modifying said chitosan through reprecipitation and deep freezing.

15. Method of strengthening hair, comprising distributing an amount sufficient for strengthening the hair of the composition according to claim 1 onto the washed, towel-dried hair, setting the hair and then drying the hair.

16. Method of treating hair, comprising distributing onto washed hair an effective amount of the composition according to claim 1, allowing said composition to work itself in, and then rinsing the hair with water.

* * * * *